E

US006913762B2

(12) United States Patent
Caplice et al.

(10) Patent No.: US 6,913,762 B2
(45) Date of Patent: Jul. 5, 2005

(54) STENT HAVING NON-WOVEN FRAMEWORK CONTAINING CELLS

(75) Inventors: Noel Caplice, Rochester, MN (US); David Berry, Santa Fe, NM (US); Robert S. Schwartz, Rochester, MN (US); David R. Holmes, Jr., Rochester, MN (US); Robert D. Simari, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 286 days.

(21) Appl. No.: 09/843,295

(22) Filed: Apr. 25, 2001

(65) Prior Publication Data

US 2002/0160033 A1 Oct. 31, 2002

(51) Int. Cl.[7] .......................... A61F 2/00; C12N 11/14; C12N 11/08; C12N 5/06; C12N 5/08
(52) U.S. Cl. .................... 424/423; 424/93.7; 435/176; 435/180; 435/395; 435/398; 435/402
(58) Field of Search ................................ 435/176, 177, 435/180, 283.1, 395, 398, 402; 424/423, 93.7

(56) References Cited

U.S. PATENT DOCUMENTS

| | | | |
|---|---|---|---|
| 3,692,618 A | | 9/1972 | Dorschner et al. |
| 4,060,081 A | | 11/1977 | Yannas et al. |
| 4,340,563 A | | 7/1982 | Appel et al. |
| 4,856,516 A | | 8/1989 | Hillstead |
| 4,973,493 A | | 11/1990 | Guire |
| 4,979,959 A | | 12/1990 | Guire |
| 4,992,226 A | | 2/1991 | Piez et al. |
| 4,994,081 A | | 2/1991 | Civerchia et al. |
| 5,002,582 A | | 3/1991 | Guire et al. |
| 5,007,934 A | | 4/1991 | Stone |
| 5,030,233 A | * | 7/1991 | Ducheyne ............... 623/16 |
| 5,034,352 A | | 7/1991 | Vit et al. |
| 5,139,941 A | | 8/1992 | Muzyczka et al. |
| 5,217,492 A | | 6/1993 | Guire et al. |
| 5,258,041 A | | 11/1993 | Guire et al. |
| 5,263,992 A | | 11/1993 | Guire |
| 5,274,074 A | | 12/1993 | Tang et al. |
| 5,312,380 A | | 5/1994 | Alchas et al. |
| 5,324,647 A | | 6/1994 | Rubens et al. |
| 5,567,612 A | * | 10/1996 | Vacanti et al. ........... 435/366 |
| 5,643,580 A | | 7/1997 | Subramaniam |
| 5,670,161 A | * | 9/1997 | Healy et al. ............. 623/1.42 |
| 5,690,670 A | * | 11/1997 | Davidson ............... 606/198 |
| 5,693,085 A | | 12/1997 | Buirge et al. |
| 5,723,003 A | | 3/1998 | Winston et al. |
| 5,725,567 A | | 3/1998 | Wolff et al. |
| 5,817,126 A | | 10/1998 | Imran |
| 5,824,043 A | * | 10/1998 | Cottone, Jr. ............. 623/1.13 |
| 5,824,049 A | | 10/1998 | Ragheb et al. |
| 5,830,879 A | | 11/1998 | Isner |
| 5,861,032 A | | 1/1999 | Subramaniam |
| 5,873,904 A | | 2/1999 | Ragheb et al. |
| 5,957,972 A | | 9/1999 | Williams et al. |
| 6,004,943 A | | 12/1999 | Shi et al. |
| 6,054,288 A | | 4/2000 | Selden et al. |
| 6,063,101 A | | 5/2000 | Jacobsen et al. |
| 6,080,177 A | | 6/2000 | Igaki et al. |
| 6,090,618 A | | 7/2000 | Parmacek et al. |
| 6,096,070 A | | 8/2000 | Ragheb et al. |
| 6,102,887 A | | 8/2000 | Altman |
| 6,156,373 A | | 12/2000 | Zhong et al. |
| 6,348,069 B1 | * | 2/2002 | Vacanti et al. ........... 623/11.11 |
| 6,455,283 B1 | * | 9/2002 | Ferrara et al. ............ 435/69.4 |

FOREIGN PATENT DOCUMENTS

| | | |
|---|---|---|
| WO | WO 97/37617 | 10/1997 |
| WO | WO 00/10620 | 3/2000 |

OTHER PUBLICATIONS

Andreansky et al., "The application of genetically engineered herpes simplex viruses to the treatment of experimental brain tumors," *Proc. Natl. Acad. Sci. USA*, 1996, 93:11313–11318.

Bhatnagar et al., "The Role in Cell Binding of a β–bend within the Triple Helical Region in Collagen α1(I) Chain: Structural and Biological Evidence for Conformational Tautomerism on Fiber Surface," *J. Biomolecular Structure & Dynamics*, 1997, 14(5):547–560.

Bhatnagar et al., "Design of Biomimetic Habitats for Tissue Engineering with P–15, a Synthetic Peptide Analogue of Collagen," *Tissue Engineering*, 1999, 5:53–65.

Felgner et al., "Enhanced Gene Delivery and Mechanism Studies with a Novel Series of Cationic Lipid Formulations," *J. Biol. Chem.*, 1994, 269(4):2550–2561.

Fletcher et al., "A steroid–triggered switch in E74 transcription factor isoforms regulates the timing of secondary–response gene expression," *Proc. Natl. Acad. Sci. USA*, 1997, 94:4582–4586.

Kay et al., "Gene therapy," *Proc. Natl. Acad. Sci. USA*, 1997, 94:12744–12746.

Lai et al., "Intercellular delivery of a herpes simplex virus VP22 fusion protein from cells infected with lentiviral vectors," *Proc. Natl. Acad. Sci. USA*, 2000, 97(21):11297–11302.

No et al., "Ecdysone–inducible gene expression in mammalian cells and transgenic mice," *Proc. Natl. Acad. Sci. USA*, 1996, 93:3346–3351.

(Continued)

*Primary Examiner*—David M. Naff
(74) *Attorney, Agent, or Firm*—Fish & Richardson P.C., P.A.

(57) ABSTRACT

Implantable medical devices that include a non-woven framework are described, as well as methods of using such devices to deliver therapeutic compounds to a patient.

3 Claims, 3 Drawing Sheets

OTHER PUBLICATIONS

Simari et al., "Requirements for Enhanced Transgene Expression by Untranslated Sequences from the Human Cytomegalovirus Immediate–Early Gene," *Mol. Med.,* 1998, 4:700–706.

Smith et al., "Adenovirus mediated expression of therapeutic plasma levels of human factor IX in mice," *Nat. Genet.,* 1993, 5:397–402.

Spector and Samaniego, "Construction and Isolation of Recombinant Adenoviruses with Gene Replacements," *Meth. Mol. Genet.,* 1995, 7:31–44.

Stadler et al., "Do Cultured Vascular Smooth Muscle Cells Resemble Those of the Artery Wall? If Not, Why Not?" *J. Cardiovasc. Pharmacol.,* 1989, 14(Suppl. 6):S1–S8.

Su et al., "Adeno–associated viral vector–mediated vascular endothelial growth factor gene transfer induces neovascular formation in ischemic heart," *Proc. Natl. Acad. Sci. USA,* 2000, 97:(25):13801–13806.

Uchida et al., "HIV, but not murine leukemia virus, vectors mediate high efficiency gene transfer into freshly isolated $G_0/G_1$ human hematopoietic stem cells," *Proc. Natl. Acad. Sci. USA,* 1998, 95:11939–11944.

* cited by examiner

STENT HAVING NON-WOVEN FRAMEWORK CONTAINING CELLS

TECHNICAL FIELD

This invention relates to implantable medical devices that include a non-woven framework, wherein the non-woven framework contains pores having an average size of at least 40 μm and metal or polymer fibers.

BACKGROUND

Implantable medical devices are used to treat various disorders. For example, stents are used to treat coronary heart disease. According to the American Heart Association, coronary heart disease is the single leading cause of death in America today. Coronary heart disease is caused by atherosclerotic narrowing of the coronary arteries and can produce angina pectoris and/or heart attack in patients. Stents can be used to open an artery that has been cleared by balloon angioplasty or as an alternative to balloon angioplasty. Typically, stents are collapsed to a small diameter, placed over an angioplasty balloon catheter, and placed in the area of the blockage. As the balloon is inflated, the stent expands and forms a scaffold to hold the artery open. The stent stays in the artery permanently, holds it open, improves blood flow to the heart muscle and relieves symptoms (usually chest pain). Restenosis or reclosing of the vessel, however, can occur in stented vessels. To help prevent restenosis, patients undergo systemic antiplatelet and anticoagulant therapy.

SUMMARY

The invention is based on implantable medical devices that include a non-woven framework. The non-woven framework provides a multi-layered, three-dimensional or lattice structure that can be coated with an extracellular matrix protein such as fibronectin to provide an excellent substrate for growth of cells that are seeded into it. Engineering of the cells in vitro that are seeded onto the device allows therapeutic compounds to be delivered to the patient in which the device is implanted. Properties of the non-woven framework allow the medical device to be expanded without compromising viability of cells growing within the framework.

In one aspect, the invention features an implantable medical device that includes a non-woven framework, wherein the non-woven framework includes metal fibers and pores having an average size of at least 40 μm, e.g., at least 60 μm. The metal fibers can be selected from the group consisting of stainless steel, tantalum, titanium, gold, and platinum. Stainless steel fibers are particularly useful. The implantable medical device further can include an extracellular matrix protein such as fibronectin. The implantable medical device can be a stent having an interior and an exterior surface, and the non-woven framework can be attached to at least a portion of the exterior surface. The stent can be fabricated from the non-woven framework.

The non-woven framework further can include cells selected from the group consisting of smooth muscle cells, fibroblasts, hepatocytes, and endothelial cells. The cells can express a polypeptide selected from the group consisting of vascular endothelial growth factor, natriuretic peptide, prostacyclin synthase, angiostatin, endostatin, erythropoietin, and a marker polypeptide.

The invention also features an implantable medical device that includes a plurality of surfaces, wherein at least a portion of at least one of the plurality of surfaces includes a non-woven framework, and wherein the non-woven framework includes pores having an average size of at least 40 μm (e.g., at least 60 μm). The non-woven framework can include metal fibers or an inert polymer such as polyethylene terephthalate or polytetrafluoroethylene. The inert polymer can be bioresorbable (e.g., polylactic acid, polyglycolic acid, or poly (N-acetyl-D-glucosamine)). The metal fibers can be selected from the group consisting of stainless steel, tantalum, titanium, gold, and platinum. Stainless steel fibers are particularly useful. The implantable medical device can be a vascular graft or a stent. The stent can be balloon expandable or self-expanding, and can be composed of stainless steel, titanium, tantalum, platinum, platinum alloys, or a nickel-titanium alloy. The non-woven framework can be fused to at least a portion of at least one of the plurality of surfaces.

The non-woven framework further can include an extracellular matrix protein such as fibronectin. The implantable medical device further can include cells selected from the group consisting of smooth muscle cells, fibroblasts, hepatocytes, and endothelial cells. The cells can express a polypeptide selected from the group consisting of vascular endothelial growth factor, natriuretic peptide, prostacyclin synthase, angiostatin, endostatin, erythropoietin, and a marker polypeptide. The cells can include a nucleic acid construct that includes a regulatory element operably linked to a nucleic acid encoding the polypeptide. The regulatory element can be inducible.

In another aspect, the invention features a non-woven framework that includes an extracellular matrix protein such as fibronectin, wherein the non-woven framework includes metal fibers and has an average pore size of at least 40 μm. The non-woven framework further can include cells selected from the group consisting of smooth muscle cells, fibroblasts, hepatocytes, and endothelial cells. The cells can express a polypeptide selected from the group consisting of vascular endothelial growth factor, natriuretic peptide, prostacyclin synthase, angiostatin, endostatin, erythropoietin, and a marker polypeptide. The cells can include a nucleic acid construct, wherein the nucleic acid construct includes a regulatory element operably linked to a nucleic acid encoding the polypeptide. The regulatory element can be inducible.

In yet another aspect, the invention features a method of delivering a polypeptide to a mammal. The method includes implanting a medical device in the mammal, wherein the medical device includes a non-woven framework. The non-woven framework includes metal fibers and pores having an average size of at least 40 μm, wherein the non-woven framework further includes an extracellular matrix protein and cells selected from the group consisting of smooth muscle cells, hepatocytes, fibroblasts, and endothelial cells, and wherein said cells express said polypeptide.

A method of delivering a polypeptide to a mammal also can include implanting a medical device in the mammal, wherein the medical device includes a plurality of surfaces, wherein a non-woven framework is attached to at least a portion of at least one of the plurality of surfaces. The non-woven framework has pores of an average size of at least 40 μm, and further includes an extracellular matrix protein and cells selected from the group consisting of smooth muscle cells, hepatocytes, fibroblasts, and endothelial cells, and wherein the cells express the polypeptide.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
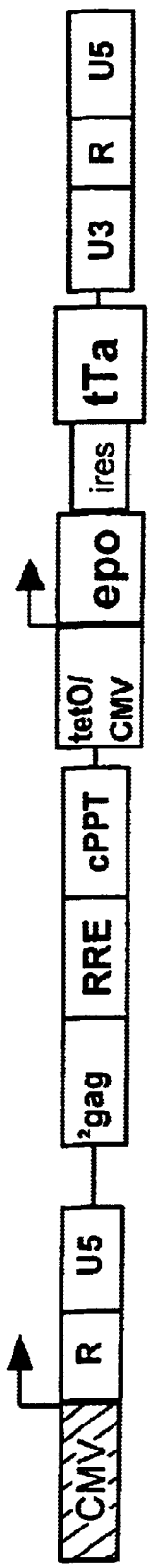
FIG. 1 is a schematic of a lentiviral tet-on vector.

Implantable medical devices of the invention include a non-woven framework. In some embodiments, the implantable medical device is fabricated from the non-woven framework such that the non-woven framework is the basis for the structure of the device. In other embodiments, the non-woven framework is attached to, e.g., adhered, coated, or welded to, at least a portion of a surface of the implantable medical device. As used herein, "non-woven framework" refers to a material having a structure of individual fibers that are interlaid in an irregular manner, e.g., a felt. In contrast, knit or woven fabrics have fibers that are interlaid in a regular manner. Non-woven frameworks can be composed of metal fibers or inert polymer fibers, and have pores of an average size of at least 40 $\mu$m (e.g., about 60 $\mu$m). Average pore size can be determined by initial bubble point pressure (American Society for Testing and Materials (ASTM) Test E128-61). Metal fibers can be formed into a non-woven framework by pressing the metal fibers on a flat surface then heating (e.g., sintering) so the fibers fuse wherever they are in contact with one another. Suitable metal fibers include stainless steel, tantalum, titanium, gold, platinum, or silver, alloys of such metals (e.g., shape-memory alloys of nickel-titanium such as Nitinol), as well as any other biocompatible metals. Stainless steel fibers are particularly useful for forming non-woven frameworks. BEKIPORE® ST AL3 from Bekaert Fibre Technologies, Zwevegem, Belgium, is an example of a useful metal non-woven framework.

Non-woven frameworks composed of inert polymers can be made by, for example, spunbound or melt blown processes. "Spunbound" refers to small diameter fibers that are "spun" by extruding molten thermoplastic material in the form of filaments from a plurality of fine, usually circular, capillaries of a spinneret, and then rapidly reducing the diameter of the extruded filaments. See, for example, U.S. Pat. Nos. 4,340,563 and 3,692,618 for a description of spunbound methods. The filaments are bonded together by passage between the rolls of a heated calender. "Melt blown" refers to a process of extruding molten thermoplastic material through a plurality of fine, typically circular, die capillaries as molten threads or filaments into a high velocity, typically heated, gas stream (e.g., air), which reduces the diameter of the filaments and deposits the filaments on a collecting surface to form a web of randomly dispersed melt-blown fibers. Inert polymers that can be used include polyethylene terephthalate and polytetrafluoroethylene (Teflon®). In some embodiments, the inert polymers are bioresorbable, e.g., polylactic acid, polyglycolic acid, and poly (N-acetyl-D-glucosamine). Alternatively, non-woven frameworks composed of inert polymers can be rapidly prototyped using stereolithography (SLA) or selective laser sintering (SLS).

The non-woven framework provides a three-dimensional structure that is suitable for cell growth. Furthermore, the non-woven framework allows close cell-cell contact, which may increase paracrine and autocrine growth factor enrichment and ensure more rapid cell colonization of the framework. Cells can be manipulated in vitro such that the cells can produce therapeutic compounds, then seeded onto the non-woven framework. Upon implantation of the medical device, the cells can expand to cover the framework and compounds produced by the modified cells are delivered both locally and systemically to the mammal. Thus, the implanted device allows therapeutic compounds to be delivered over an extended period of time. For example, it may be desirable to deliver the therapeutic compound to the mammal for two or more weeks, e.g., three, four, five, six, seven, or eight or more weeks. In some embodiments, the device itself is used to treat a mammal (e.g., stent a diseased vessel), while therapeutic compounds are being delivered.

Implantable Medical Devices

As described above, implantable medical devices of the invention include a non-woven framework. The term "implantable medical device", as used herein, includes any medical device that is suitable for implantation in a mammal, and in particular, in a human. Non-limiting examples of implantable medical devices include vascular grafts and stents. Vascular grafts are tubular structures that can be used within the body to bypass blocked or diseased vessels. Stents are used within the body to restore or maintain the patency of a body lumen. For example, stents can be used in blood vessels, the urinary tract, or in the bile duct to treat these body structures when they have weakened. With blood vessels, stents typically are implanted therein to treat narrowings or occlusions caused by disease, to reinforce the vessel from collapse, or to prevent the vessel from abnormally dilating (e.g., an aneurysm).

A stent typically has a tubular structure defining an inner channel that accommodates flow within the body lumen. The outer walls of the stent engage the inner walls of the body lumen. Positioning of a stent within an affected area can help prevent further occlusion of the body lumen and permit continued flow. A stent typically is deployed by percutaneous insertion of a catheter or guide wire that carries the stent. The stent ordinarily has an expandable structure. Upon delivery to the desired site, the stent can be expanded with a balloon mounted on the catheter. See, for example, U.S. Pat. No. 4,856,516 for a description of a typical stent and a method for its deployment and placement with a balloon catheter. Alternatively, the stent may have a biased or elastic structure that is held within a sheath or other restraint in a compressed state. The stent expands voluntarily when the restraint is removed. In either case, the walls of the stent expand to engage the inner wall of the body lumen, and generally fix the stent in a desired position.

A variety of methods can be used to fabricate vascular grafts or stents from a non-woven framework. For example, a metal non-woven framework can be cut, for example, by lasers, electro-discharge machining, or plasma cutting. Electron beam welding, gas tungsten arc welding, plasma welding, spot welding, laser welding, and ultrasonic welding are examples of welding techniques can be used to bond a metal non-woven framework. A metal non-woven framework also can be adhesively bonded.

Alternatively, the non-woven framework can be attached to at least a portion of at least one surface of an implantable medical device, e.g., attached to a portion of an exterior or interior surface of a stent. The non-woven framework can be attached to any implantable medical device made of a biocompatible material that has the necessary structural and mechanical attributes. For example, the non-woven framework can be attached to a vascular graft composed of an inert, biocompatible material such as polytetrafluoroethylene (Teflon®) or to a stent formed from metals such as gold, silver, platinum, stainless steel, tantalum, titanium, shape-memory alloys such as nickel-titanium alloys, e.g., Nitinol, as well as synthetic and natural polymers such as polyethylene, polypropylene, polytetrafluoroethylene (Teflon®), including biodegradable polymers such as polyglycolic acid, polylactic acid, and poly (N-acetyl-D-glucosamine). Such materials can be selected or coated to provide radio-opacity, if desired. Non-woven frameworks also can be attached to stents formed from ceramic materials such as calcium phosphate, alumina or bioglass, as well as composite materials. In particular, the non-woven framework can be attached, for example, to a Wiktor® stent (Medtronic), Bx VELOCITY stent (Cordis Corporation), or GR II® stent (Cook Incorporated).

The non-woven framework can be attached to a medical device by known methodologies including, for example, coating, welding techniques including electron beam welding, gas tungsten arc welding, plasma welding, spot welding, laser welding, and ultrasonic welding, or adhering the non-woven framework to an implantable medical device such as a stent. In particular, one or more strips of a non-woven framework can be attached over the length of the stent (i.e., the longitudinal axis of the stent) or around the circumference of the stent by spot-welding. With polymer non-woven frameworks, the material can be adhered to the stent.

Implantable medical devices of the invention further can include an extracellular matrix protein (ECMP) or combinations of ECMPs. Non-limiting examples of ECMPs include fibronectin, vitronectin, and collagen. Fibronectin is particularly useful. Typically, an ECMP is applied as a solution containing about 5 to 250 µg/ml of ECMP in a buffer or culture medium, e.g., about 40 µg/ml to about 70 µg/ml of an ECMP. In addition, other agents such as antibiotics or growth factors can be included with the fibronectin. The solution of ECMP can be applied to a portion of or over the entire exterior surface of an implantable medical device using conventional application techniques, such as dipping, spraying, brushing, or sponging. For example, the ECMP can be applied to the non-woven framework attached to the medical device. The liquid vehicle can be removed from the implantable medical device by, for example, air-drying, to provide an essentially dry coating of the ECMP on the surface of the device.

Delivery of Polypeptides

Implantable medical devices of the invention can be used to deliver polypeptides and other therapeutic compounds to a mammal, and in particular to a human patient. In general, a medical device of the invention is seeded with cells such as smooth muscle cells, fibroblasts, hepatocytes, endothelial cells, or stem cells in vitro then implanted in a patient. Typically, cells are harvested from the patient in which the medical device will be implanted. In some embodiments, however, cells can be harvested from a donor of the same or of a different species that is not the recipient of the medical device. For example, it may be useful to harvest cells from a pig for transplantation in a human.

Tissue or other biological sample can be harvested from the patient by routine procedures. For example, endothelial cells can be obtained from fat tissue. See, for example, U.S. Pat. No. 5,312,380. Smooth muscle cells can be isolated from the human saphenous vein, which is easily accessible by surgery. Stem cells can be isolated from bone marrow. Hepatocytes and fibroblasts can be isolated from biopsy material. Smooth muscle cells are particularly useful as they are easy to harvest and subsequently expand in vitro, and are robust in culture. Primary cell cultures can be established by enzymatically digesting the harvested tissue (e.g., with trypsin, collagenase, elastase, or the like) or explanting the tissue. Primary cell culture refers to the first plating of the cells, and includes cells that are in suspension. Secondary cultures are used to expand the number of cells and are generated upon replating or passaging the primary cell culture.

Typically, cells that are seeded onto the medical device are modified such that the cells produce one or more polypeptides or other therapeutic compounds of interest. As used herein, the term "polypeptide" refers to any chain of amino acids, regardless of length or post-translational modification. Such polypeptides can be secreted into the vasculature or can produce therapeutic compounds that can be secreted into the vasculature. Therapeutic compounds include small molecules produced by polypeptides (e.g., prostaglandins or nitric oxide (NO)), as well as ribozymes and antisense nucleic acids. As a result, the implantable medical device can deliver any polypeptide or any therapeutic compound to the mammal for treating any disease, including vascular and renal diseases as well as various cancers. In addition, marker polypeptides can be delivered to a patient to aid in diagnostic testing.

For example, to treat cardiovascular disease, cells can be engineered to produce cell mitogens such as vascular endothelial growth factor (VEGF) or fibroblast growth factor-4 (FGF-4), vasopressin, atrial natiuretic peptide, and combinations of such polypeptides and seeded onto a medical device, which then is implanted in a patient. In particular, a stent containing engineered cells that secrete VEGF can be used to treat patients with peripheral vascular disease, distal coronary disease, or chronic total occlusions unsuitable for conventional revascularization approaches. Expression of prostacyclin synthase, which produces prostacyclin ($PGI_2$) from prostaglandin $H_2$ ($PGH_2$), in cells can result in delivery of $PGI_2$ to tissues and can be used for relaxing vascular smooth muscle. Expression of nitric oxide synthase, which catalyzes the production of NO, in cells can result in delivery of NO to tissues and can be used, for example, to inhibit restenosis. Anti-angiogenic polypeptides such as angiostatin and endostatin can be used to aid in the treatment of angiogenic dependent tumors and micrometastases in patients. A similar strategy can be used to aid treatment of biliary duct tumors. Hematopoietic growth factors such as erythropoietin (EPO), granulocyte/macrophage colony stimulating factor (GM-CSF), and interleukins can be used to increase production of blood cells. For example, EPO can be used to stimulate red cell production and to treat anemia.

To modify the isolated cells such that the polypeptide or other therapeutic compounds of interest are produced, the appropriate exogenous nucleic acid must be delivered to the cells. Primary cultures or secondary cell cultures can be modified then seeded onto the device. In some embodiments, transient transformants in which the exogenous nucleic acid is episomal, i.e., not integrated into the chromosomal DNA, can be seeded onto the medical device. Preferably, stable transformants, i.e., the exogenous nucleic acid is integrated into the host cell's chromosomal DNA, are selected. The term "exogenous" as used herein with reference to a nucleic acid and a particular cell refers to any nucleic acid that does not originate from that particular cell as found in nature. In addition, the term "exogenous" includes a naturally-occurring nucleic acid. For example, a nucleic acid encoding a polypeptide that is isolated from a human cell is an exogenous nucleic acid with respect to a second human cell once that nucleic acid is introduced into the second human cell.

The exogenous nucleic acid can be transferred to the cells within the primary or secondary culture using recombinant viruses that can infect cells, or liposomes or other non-viral methods such as electroporation, microinjection, or calcium phosphate precipitation, that are capable of delivering nucleic acids to cells. In either case, the exogenous nucleic acid that is delivered typically is part of a vector in which a regulatory element such as a promoter is operably linked to the nucleic acid of interest. The promoter can be constitutive or inducible. Non-limiting examples of constitutive promoters include cytomegalovirus (CMV) promoter and the Rous sarcoma virus promoter. As used herein, "inducible" refers to both up-regulation and down regulation. An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent such as a protein, metabolite, growth regulator, phenolic compound, or a physiological stress imposed directly by, for example heat, or indirectly through the action of a pathogen or disease agent such as a virus. The inducer also can be an illumination agent such as light and light's various aspects, which include wavelength, intensity, fluorescence, direction, and duration.

An example of an inducible promoter is the tetracycline (tet)-on promoter system, which can be used to regulate transcription of the nucleic acid. In this system, a mutated Tet repressor (TetR) is fused to the activation domain of herpes simplex VP 16 (transactivator protein) to create a tetracycline-controlled transcriptional activator (tTA), which is regulated by tet or doxycycline (dox). In the absence of antibiotic, transcription is minimal, while in the presence of tet or dox, transcription is induced. Alternative inducible systems include the ecdysone or rapamycin systems. Ecdysone is an insect molting hormone whose production is controlled by a heterodimer of the ecdysone receptor and the product of the ultraspiracle gene (USP). Expression is induced by treatment with ecdysone or an analog of ecdysone such as muristerone A.

Additional regulatory elements that may be useful in vectors, include, but are not limited to, polyadenylation sequences, translation control sequences (e.g., an internal ribosome entry segment, IRES), enhancers, or introns. Such elements may not be necessary, although they may increase expression by affecting transcription, stability of the mRNA, translational efficiency, or the like. Such elements can be included in a nucleic acid construct as desired to obtain optimal expression of the nucleic acids in the cell(s). Sufficient expression, however, may sometimes be obtained without such additional elements.

Other elements that can be included in vectors include nucleic acids encoding selectable markers. Non-limiting examples of selectable markers include puromycin, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Such markers are useful for selecting stable transformants in culture.

Viral vectors that can be used include adenovirus, adeno-associated virus (AAV), retroviruses, lentiviruses, vaccinia virus, measles viruses, herpes viruses, and bovine papilloma virus vectors. See, Kay et al. (1997) *Proc. Natl. Acad. Sci. USA* 94:12744–12746 for a review of viral and non-viral vectors. Viral vectors are modified so the native tropism and pathogenicity of the virus has been altered or removed. The genome of a virus also can be modified to increase its infectivity and to accommodate packaging of the nucleic acid encoding the polypeptide of interest.

Adenoviral vectors can be easily manipulated in the laboratory, can efficiently transduce dividing and nondividing cells, and rarely integrate into the host genome. Smith et al. (1993) *Nat. Genet.* 5:397–402; and Spector and Samaniego (1995) *Meth. Mol. Genet.*, 7:31–44. The adenovirus can be modified such that the E1 region is removed from the double stranded DNA genome to provide space for the nucleic acid encoding the polypeptide and to remove the transactivating E1a protein such that the virus cannot replicate. Adenoviruses have been used to transduce a variety of cell types, including, inter alia, keratinocytes, hepatocytes, and epithelial cells.

Adeno-associated viral (AAV) vectors demonstrate a broad range of tropism and infectivity, although they exhibit no human pathogenicity and do not elicit an inflammatory response. AAV vectors exhibit site-specific integration and can infect non-dividing cells. AAV vectors have been used to deliver nucleic acid to brain, skeletal muscle, and liver over a long period of time (e.g., >9 months in mice) in animals. See, for example, U.S. Pat. No. 5,139,941 for a description of AAV vectors.

Retroviruses are the most-characterized viral delivery system and have been used in clinical trials. Retroviral vectors mediate high nucleic acid transfer efficiency and expression. Retroviruses enter a cell by direct fusion to the plasma membrane and integrate into the host chromosome during cell division.

Lentiviruses also can be used to deliver nucleic acids to cells, and in particular, to non-dividing cells. Replication deficient HIV type I based vectors have been used to transduce a variety of cell types, including stem cells. See, Uchidda et al. (1998) *Proc. Natl. Acad. Sci. USA* 95:11939–11944. FIG. 1 provides an example of a lentiviral tet-on vector that is useful in the invention.

Non-viral vectors can be delivered to cells via liposomes, which are artificial membrane vesicles. The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Transduction efficiency of liposomes can be increased by using dioleoylphosphatidylethanolamine during transduction. See, Felgner et al. (1994) *J. Biol. Chem.* 269:2550–2561. High efficiency liposomes are commercially available. See, for example, SuperFect® from Qiagen (Valencia, Calif.).

Cells can be seeded onto the medical device in a suitable culture medium, cultured to a sufficient density of cells is obtained, and then the seeded device can be implanted in the patient upstream in the vasculature from the disease target (e.g., upstream from the arterial supply of a tumor) or within a diseased or weakened vessel. Cells can be seeded at a density ranging from approximately $1 \times 10^5$ to $7.5 \times 10^5$ cells/$cm^2$ of non-woven framework. For example, cells can be seeded at $1 \times 10^5$ or $2 \times 10^5$ cells/$cm^2$ of non-woven framework. High cell density (e.g., $5 \times 10^5$ cells/$cm^2$ non-woven framework) can be achieved in vitro within one to six weeks of seeding onto the framework. Cells seeded at $2 \times 10^5$ cells/$cm^2$ can cover the non-woven framework within 10 days.

As described herein, expression of green fluorescence protein (GFP) was observed at least four weeks after implanting a stent into a pig's coronary artery, where the stent contained a non-woven framework attached to a portion of the outer surface and transfected porcine smooth muscle cells seeded onto the non-woven framework. Human smooth muscle cells, obtained from discarded human saphenous vein, also have been used, and were at a high density 4–6 weeks post seeding. Production of polypeptides or other therapeutic compounds in a mammal can be monitored using known methods, e.g., imaging techniques, immunoassays, or functional assays.

The invention will be further described in the following examples, which do not limit the scope of the invention described in the claims.

EXAMPLES

Example 1

Cell-based Delivery Material

Cultured autologous smooth muscle cells were chosen as the target for cell-based gene transfer. Vascular smooth muscle cells were obtained from the porcine carotid artery and established in primary culture as previously described by Stadler et al. (*J. Cardiovasc. Pharmacol.*, 1989, 14 Suppl6:S1–8). After establishing secondary cultures (passages 2–6) of the smooth muscle cells, the cells were seeded onto a non-woven, stainless steel framework from Bekaert Fibre Technologies, Zwevegem, Belgium (Catalog No BEKIPORE® ST AL3). Initial experiments were performed to test whether precoating the non-woven framework (5 mm×20 mm) with a extracellular matrix protein increased growth of cells seeded onto the framework.

Briefly, strips of the non-woven framework were sterilized in 100% ethanol for 1 hour at room temperature. The ethanol was removed and that remaining allowed to evaporate. The non-woven framework then was coated with fibronectin (Sigma, 50 mg/ml), vitronectin (Sigma, 50 mg/ml), or collagen (Sigma, 50 mg/ml) diluted in serum free medium 199 and air dried in a sterile fume-hood overnight at room temperature. Cell growth was compared. Fibronectin caused approx $5 \times 10^5$ cells/$cm^2$ to grow onto the stainless steel framework, whereas vitronectin and collagen had a minimal effect on cell growth with seeding of 0.4 and $0.5 \times 10^5$ cells/$cm^2$ respectively.

Growth of cells also was compared between cells seeded onto fibronectin coated and onto uncoated non-woven frameworks. Smooth muscle cells were seeded at a density of $2 \times 10^5$ cells per piece of non-woven framework material (both fibronectin coated and uncoated). Cells within the framework were analyzed at various times after initial seeding (4, 7, and 14 days) using scanning electron microscopy to determine the pattern of cell colonization. Cells in the non-woven framework were fixed in formalin and washed prior to plastic embedding for scanning electron microscopy. The number of cells retained on the non-woven framework after 14 days in culture was calculated by trypsin-EDTA removal followed by counting of the cells on a hemocytometer. Initial migration of cells was along the crosswires of the non-woven framework and subsequent cell migration across the interwire spaces after 1 week in culture. By day 14, the framework was almost completely colonized and a multilayered cellular tissue was formed. Precoating the framework with fibronectin caused a significant increase (>20-fold) in cell seeding and retention at 2 weeks within the framework in vitro (fibronectin coated, $4.9 \pm 0.4 \times 10^5$ cells/$cm^2$ versus uncoated, $0.2 \pm 0.03 \times 10^5$ cells/$cm^2$. P<0.001).

Example 2

In Situ Cell Growth Within a Non-woven Framework

When cells were grown within the non-woven framework, it was technically difficult to process this tissue for conventional immunohistochemistry as the framework could only be cut after embedding in plastic. Furthermore, the cross-over lattice structure of the non-woven framework precluded adequate cell visualization using standard light microscopy. To overcome this, an in situ cell identification method was developed using enface preparation of the seeded non-woven framework, followed by fixation, immunofluorescence and subsequent analysis using confocal microscopy. This system also allowed in situ visualization of cell-associated antigens.

Early passage smooth muscle cells were again seeded at a density of $2 \times 10^5$ cells per coated non-woven framework and allowed to colonize the material for two weeks as described above. The seeded non-woven framework then was removed from medium, washed with PBS, and fixed in cold methanol (−20° C.) for 10 minutes. Individual cells were identified by staining cell nuclei with propidium iodide for 10 minutes and visualized with confocal microscopy. Identification of cells as smooth muscle cell origin was confirmed using α-smooth muscle actin primary and fluoroscein (FITC) labeled secondary antibodies. Positive immunofluorescence was visualized using confocal microscopy. Cells were visible in stained tissue from 2 weeks in culture.

Example 3

In vitro Gene Transfer of Cells in Felt

Once feasibility of seeding with multiple layers of porcine smooth muscle cells was demonstrated, experiments were performed to determine whether these cells could be transduced with a reporter gene encoding a cell associated protein (green fluorescence protein, GFP) or a gene encoding a secreted protein (tissue factor pathway inhibitor, TFPI).

Figure 2:
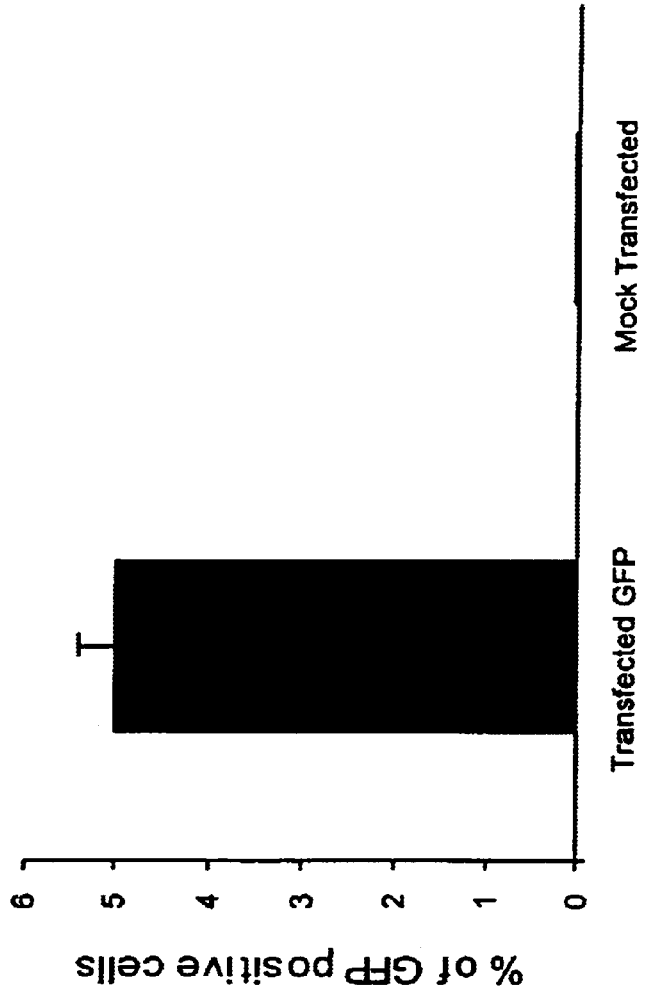
FIG. 2 is a graph of the percentage of GFP positive cells in fibronectin coated felt following liposomal transfection with GFP plasmid and mock transfection.

Initial in vitro gene transfer experiments were performed using a cationic liposome-GAP DLRIE/DOPE, which was previously characterized. See, Simari et al., *Mol. Med.* 1998, 4(11):700–706. Secondary cultured smooth muscle cells were seeded at $2\times10^5/cm^2$ within the non-woven framework for 1 week so that the cells could reach approximately 50% confluence. Cells were washed twice in PBS before adding the DNA liposome solution. DNA liposomes were prepared by adding 10 μg of plasmid DNA (either GFP or TFPI) to 0.5 ml of Opti-MEM (Gibco/BRL) or 1 μg of plasmid DNA to 10 μl Superfect (Qiagen). A cationic lipid was prepared by adding 10 μg of GAP DLRIE/DOPE (Vical) to 0.5 ml of Opti-MEM. Prior to transfection, the DNA solution was added to the liposomes and gently mixed. The transfection solution was mixed with M199 containing 10% fetal calf serum and penicillin (100 u/ml), streptomycin sulfate (100 μg/ml), and L-glutamine (2 mM), then incubated with two seeded strips of non-woven framework for 2 hours at 37° C. Following transfection, the seeded cells were washed twice and serum-enriched medium replaced. GFP transgene expression within the seeded cells was analyzed at 72 hours after transfection using confocal microscopy to identify cellular GFP expression. Approximately 5% of cells were seen to express GFP when counted as a percentage of total propidium iodide staining cells (FIG. 2) using a computerized image analysis system.

Figure 3:
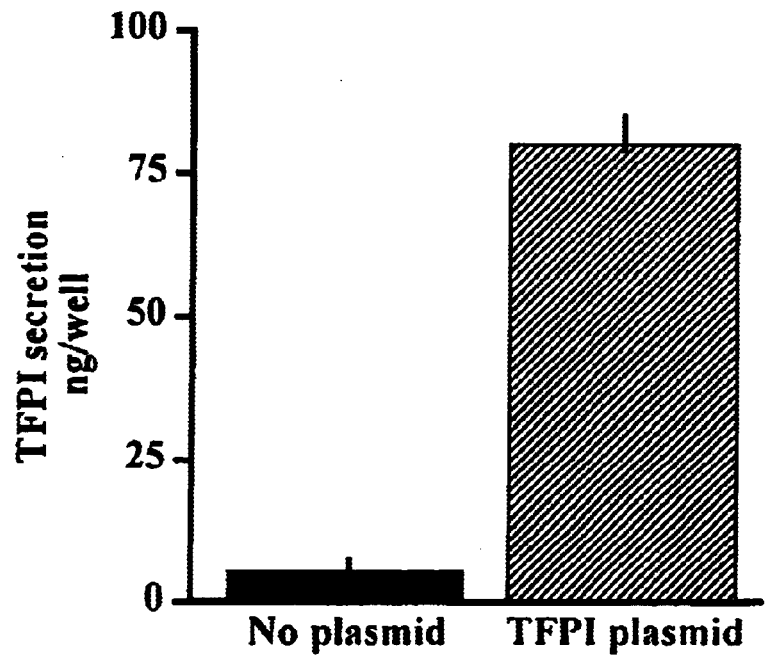
FIG. 3 is a graph of the levels of secreted TFPI antigen in the conditioned medium of cells transfected with liposome and TFPI plasmid (hatched bar) compared to mock transfected cells (solid bar). TFPI antigen was measured using a commercially available ELISA kit.

Similar liposome transfection experiments were performed using TFPI plasmid DNA. To quantitate the levels of secreted TFPI antigen in transfected cells, conditioned media from TFPI transfected and mock-transfected cells were assayed using a sandwich ELISA (American Diagnostica). TFPI antigen levels in the conditioned medium increased 20 fold in TFPI transfected compared to mock-transfected cells (FIG. 3).

Example 4

In vivo Delivery of Stent with Felt-backbone

Experiments were performed to test feasibility of in vivo deployment of a stent having a non-woven framework backbone in the porcine coronary circulation. Further experiments examined the retention of seeded cells within this modified stent in vivo and assessed the vascular and hematologic response to seeded stent implantation.

The non-woven framework was engineered as a backbone on a conventional stent (Wiktor design) to test the efficacy of percutaneous deployment of this cellular scaffold and fibronectin coated as described above. Briefly, a piece of non-woven framework was sheared to a rectangle equal in length to a 20 mm Wiktor stent, and of a width roughly one fourth the circumference of the stent when expanded (~1 $cm^2$ area). The rectangle piece of non-woven framework was clamped between two pieces of 3 mm thick copper plate and the exposed edges of the mesh were sequentially heated to a melting point with a gas tungsten arc welding torch to seal the edges so that there were no sharp, exposed fibers. Copper plates were used as a heat sink to prevent catastrophic melting of the medium by the exposed plasma from the torch. The Wiktor wire stent was expanded with a balloon to the appropriate size, and the rectangle of the mesh was clamped to the periphery of the stent with both long axes matching. The mesh then was fused to the tantalum wire using two custom designed spot welding electrodes. The stent assembly was ultrasonically cleaned several times in absolute ethanol. Before seeding with cells, the stent was washed in 25 ml Haemo-Sol (4.3 g/250 ml water) for 30 minutes with rocking, rinsed several times in filtered sterile water, washed in absolute alcohol, and gas sterilized. The stent was coated in 200 ml fibronectin (50 mg/cm²) and allowed to air-dry overnight under sterile laminar flow conditions.

Initial animal experiments were performed to examine the in vivo vascular response to stent placement in the porcine coronary artery. At 4 days following implantation, the cells had formed a multilayered tissue completely covering the non-woven framework with only the cut wires of the conventional stent exposed.

In another experiment, stents with a fibronectin coated non-woven framework backbone were deployed over a balloon in the left anterior coronary artery of pigs. No significant neo-intimal response was noted at 4 weeks following stent placement at a 1:1 balloon-artery ratio.

Figure 4:
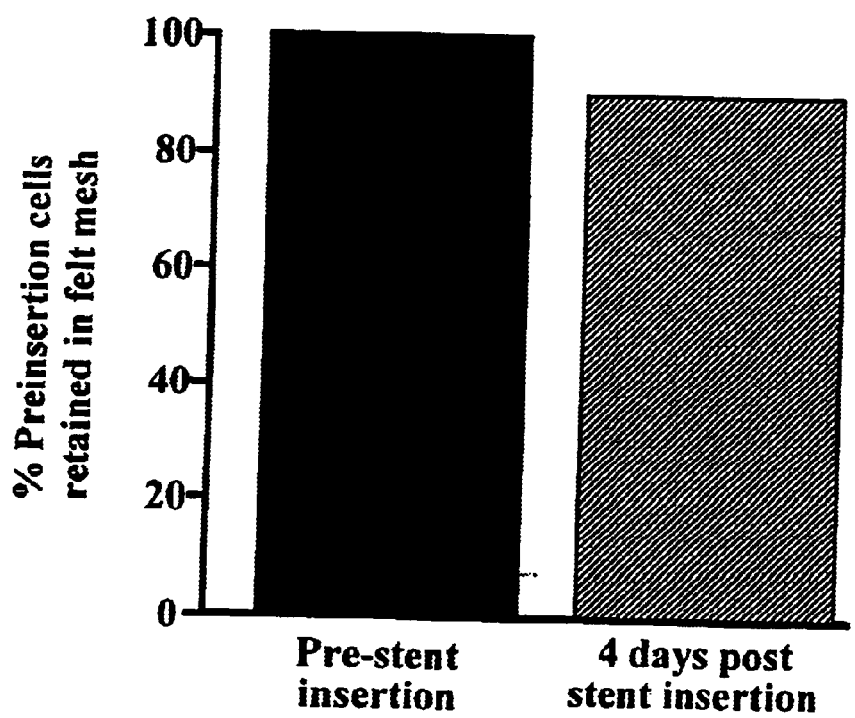
FIG. 4 is a graph of seeded smooth muscle cell retention within the felt backbone pre- and 4 days post-stent insertion. Retention is expressed as a percentage of the number of cells in the stent pre-insertion (n=3).

Experiments then were performed to determine the feasibility of in vivo gene transfer using this delivery system. Smooth muscle cell retention on the stent in vivo was initially examined. Briefly, autologous smooth muscle cells were obtained from the carotid artery of a pig and enzyme digested using collagenase and elastase, subcultured, and subsequently seeded in the non-woven framework backbone of several stents as described above. The seeded stents were then analyzed for cell retention by comparing cell numbers within the non-woven framework obtained by trypsin removal pre and 4 days post coronary artery stent implantation. Approximately 90% (92±4%, n=3) of the cells were retained within the non-woven framework at 4 days in vivo (FIG. 4) suggesting that only small numbers of cells were removed at the time of stent deployment.

Example 5

In Vivo Cell-based Gene Delivery Using Stent with Felt Backbone

In vivo reporter gene delivery was examined in the porcine coronary vasculature using the seeded felt stent. Cells seeded within the non-woven framework of the stent were again liposome transfected (GAP-DLRIE-DOPE) using GFP DNA plasmid (as described above), 24 hours prior to stent implantation in the porcine coronary artery. In vivo GFP expression then was analyzed at 4 days after stent deployment using en face confocal analysis of the cells within the non-woven framework. The non-woven framework backbone of the stent was fixed with 2% paraformaldehyde prior to laying enface and imaging with confocal microscopy. Approximately 5% of the cells within the non-woven framework were positive for GFP expression. GFP expression at similar levels was also seen at 4 weeks following stent implantation.

Figure 5:
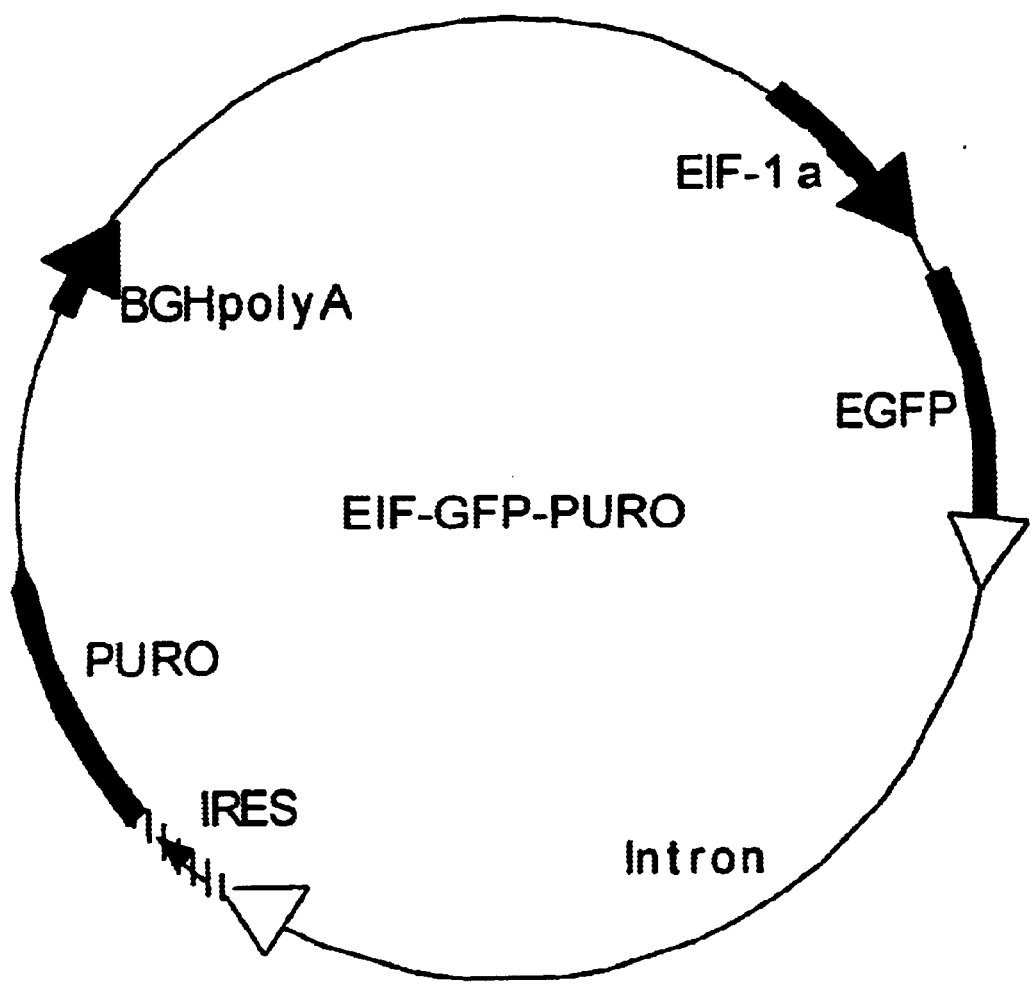
FIG. 5 is a schematic of a polycystronic GFP plasmid vector with an elongated factor 1a promoter and linked by IRES to a puromycin resistance gene

To increase the efficiency of transduction, primary cultures of porcine vascular smooth muscle cells were used that had been taken from a 2–3 cm segment of a porcine external jugular vein and in first passage. Cells were enzyme dispersed from the media and intima of a vessel following removal of the adventitia and endothelium. Early passage pSMC (PI) were transiently transfected with a plasmid encoding the GFP gene and a puromycin resistance gene (Irespuro-GFP, see FIG. 5), followed by selection in puromycin and seeding onto the stent containing the non-woven framework. Cells were seeded at a density of $1\times10^5$ cells/$cm^2$ of non-woven framework in a 6-well tissue plate. Following cell seeding, culture medium was changed every third day for two to four weeks at which time the cells had reached near confluence on the non-woven framework.

Seeded GFP positive cells within the non-woven framework were treated for 48 hours with heparin (100 μg/ml) before stent placement.

Seeded stents were deployed over a balloon in the right coronary and left anterior descending coronary arteries of pigs via an external carotid cut-down approach under angiographic guidance. The balloon-artery diameter ratio was 1.1:1 at maximum inflation. The animals were fed a normal chow diet for four weeks following stent deployment, at which time they were sacrificed. Coronary angiograms were performed on each pig before sacrifice to assess luminal narrowing within the stent.

Stable transfection of 100% of primary passage one jugular vein smooth muscle cells with a GFP plasmid containing a puromycin resistance gene and subsequent seeding onto the mesh resulted in ~95%GFP expression by confocal microscopy and FACS analysis. Coronary angiography at four weeks confirmed all the stents to be patent with minimal luminal narrowing. Plastic embedded transverse sections through the mesh stent four weeks post implantation showed a widely patent vessel lumen with minimal intimal hyperplasia at the site of the mesh. No evidence of inflammatory infiltrate at the site of seeded cells was observed by histological analysis. At four weeks, GFP expressing cells were uniformly distributed throughout the mesh. These cells were confirmed as smooth muscle origin by positive staining for α smooth muscle actin. Analysis of the number of GFP positive cells retained within the non-woven framework at four weeks post implantation showed no significant gain or loss of GFP positive cells compared to pre-implantation. Analysis of adjacent vessel wall showed no evidence of migration of GFP positive cells into the surrounding vessel wall.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An implantable medical device comprising a stent, a non-woven framework attached to said stent, and in vitro seeded cells within said non-woven framework, wherein said non-woven framework comprises stainless steel fibers and pores having an average size of at least 40 μm, wherein said non-woven framework is not coated with an extracellular matrix protein, and wherein said implantable medical device is implantable within the vascular system of a mammal via percutaneous deployment.

2. The implantable medical device of claim 1, wherein said cells express a polypeptide selected from the group consisting of vascular endothelial growth factor, natriuretic peptide, prostacyclin synthase, angiostatin, endostatin, erythropoietin, and a marker polypeptide.

3. The implantable medical device of claim 1, wherein said stent is balloon expandable or self-expanding.

* * * * *